United States Patent [19]

Steffee

[11] Patent Number: 5,071,437
[45] Date of Patent: Dec. 10, 1991

[54] ARTIFICIAL DISC

[75] Inventor: Arthur D. Steffee, Moreland Hills, Ohio

[73] Assignee: AcroMed Corporation, Cleveland, Ohio

[21] Appl. No.: 617,923

[22] Filed: Nov. 21, 1990

Related U.S. Application Data

[63] Continuation of Ser. No. 311,619, Feb. 15, 1989, abandoned.

[51] Int. Cl.⁵ ............................................. A61F 2/44
[52] U.S. Cl. ........................................ 623/17; 606/61
[58] Field of Search ............................. 623/17; 606/61

[56] References Cited

U.S. PATENT DOCUMENTS

| | | | |
|---|---|---|---|
| 3,867,728 | 2/2975 | Substad et al. | |
| 4,309,777 | 1/1982 | Patil | 128/92 YM |
| 4,714,469 | 12/1987 | Kenna | 128/92 YM |
| 4,743,256 | 5/1988 | Brantigan | |
| 4,759,766 | 7/1988 | Buettner-Janz et al. | |
| 4,874,389 | 10/1989 | Downey | 623/17 |
| 4,911,718 | 3/1990 | Lee et al. | 623/17 |
| 4,917,704 | 4/1990 | Frey et al. | 623/17 |

FOREIGN PATENT DOCUMENTS

| | | | |
|---|---|---|---|
| 0298235 | 5/1988 | European Pat. Off. | |
| 0317972 | 11/1988 | European Pat. Off. | |
| 0356112 | 8/1989 | European Pat. Off. | |
| 3023353 | 4/1981 | Fed. Rep. of Germany | 623/17 |
| 1122634 | 5/1956 | France | |
| 0895433 | 1/1982 | U.S.S.R. | 623/17 |

OTHER PUBLICATIONS

McMillin, PHD, "Characterization of Hexsyn, a Polyolefin Rubber", Jul. 1987, vol. 2, Journal of Biomaterials Applications.
Journal of Biomaterials Applications Article.

Primary Examiner—David J. Isabella
Assistant Examiner—Stephanie L. Iantorno
Attorney, Agent, or Firm—Tarolli, Sundheim & Covell

[57] ABSTRACT

A spinal disc prosthesis comprises an upper flat rigid plate, a lower flat rigid plate, and a flat elastomeric core interposed between said plates and adhered to the plates. A plurality of spaced-apart protuberances extend outwardly from the exposed faces of the plates for engagement with vertebrae above and below the plates. A porous coating covers the exposed surfaces of the plates. The elastomeric core is made of a polyolefin rubber having mechanical properites similar to a natural spinal disc.

6 Claims, 2 Drawing Sheets

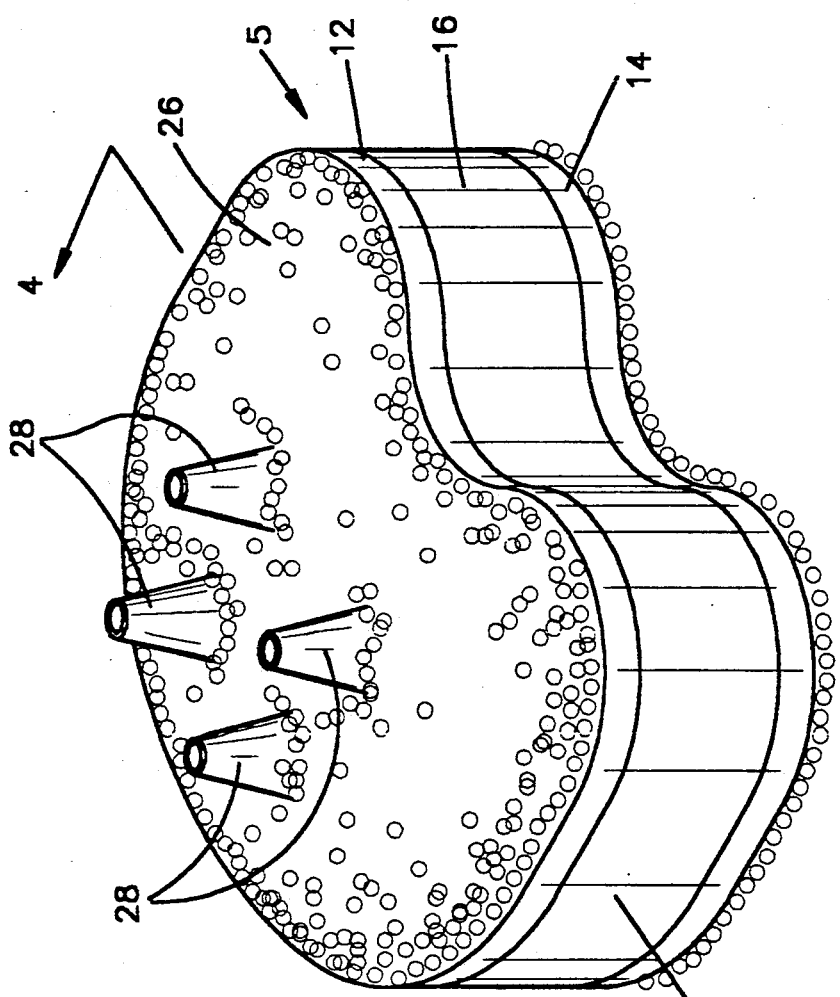
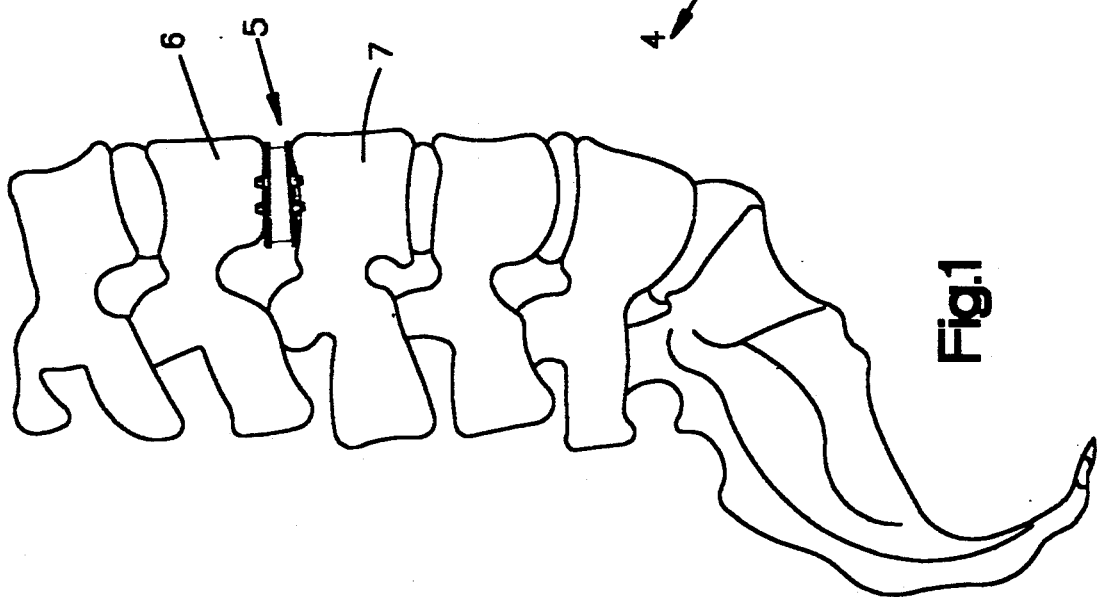
Fig.2
Fig.1

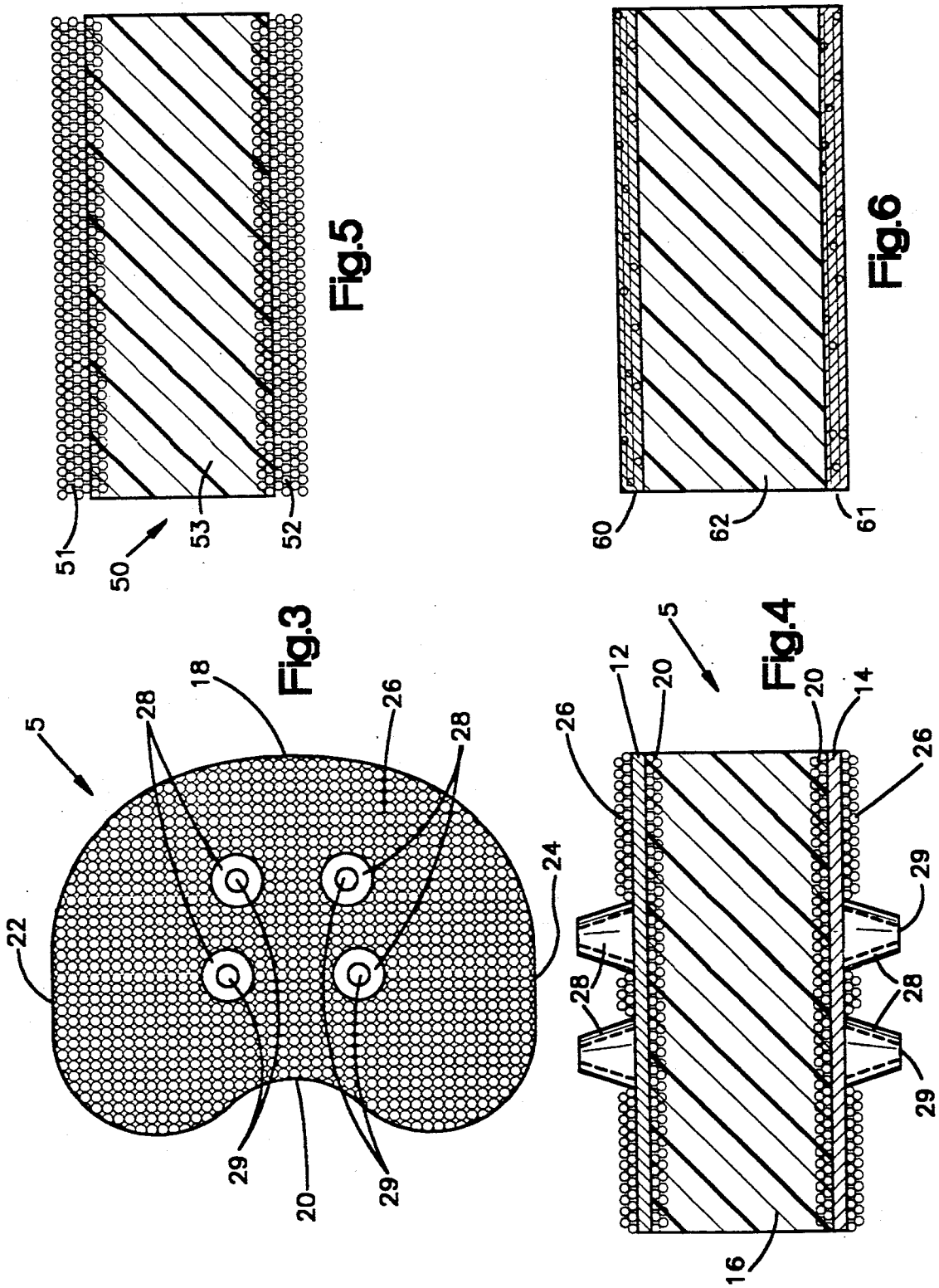

ARTIFICIAL DISC

This is a continuation of co-pending application Ser. No. 07/311,619, filed on Feb. 5, 1989, now abandoned.

BACKGROUND OF THE INVENTION

1. Technical Field

The present invention relates to an artificial spinal disc or prosthesis to replace a damaged or degenerated spinal disc.

2. Description of the Prior Art

An artificial spinal disc desirably should be capable of acting as a natural disc. The artificial disc should maintain the vertebrae spaced from each other and prevent pinching of nerves or spinal cord. The artificial disc should carry load and transmit load between the vertebrae adjacent the disc with an even distribution of the load across the disc. Further, the artificial disc should be sufficiently resilient to enable relative turning (flexion) of the vertebrae adjacent the disc (as upon turning of the shoulders of the patient having the disc). Research has shown that a natural spinal disc enables angular flexion between 2° and 3°. The artificial disc must also provide resistance to turning as does a natural disc so that excessive turning of one vertebra relative to the other is not possible. Also, the artificial disc should be resilient to accommodate all other motions of the spine including flexion, extension, lateral bending as well as combinations of these motions. Again, excessive motion of one vertebra relative to another should not be possible. The artificial disc should be both biocompatible and biostable such that the disc itself or any of its degradation by products, if any exist, do not cause adverse tissue reactions.

U.S. Pat. No. 3,867,728 discloses a prosthetic spinal disc which in one form comprises a reinforced resilient block of elastomer, such as silicone rubber or polyurethane. The elastomer is reinforced by fibrous material such as Dacron filaments embedded in the silicone elastomer. The upper and lower surfaces of the disc can be open-pore, tissue-ingrowth receptive surfaces.

Prior U.S. Pat. No. 4,309,777 discloses an artificial spinal disc comprising upper and lower disc portions of a metal such as stainless steel. The disc portions are held in a spaced-apart relationship by a plurality of compression springs. A plurality of spikes extend upwardly and downwardly from the exposed surfaces of the disc portions. The springs can be varied in size and number to vary the size of the disc had to achieve a desired vertebra separation.

Prior U.S. Pat. No. 4,714,469 discloses a spinal implant comprising a rigid solid body having opposed upper and lower surfaces, elongated protuberances of substantially semi-circular cross section extending the full width of the upper and lower surfaces, and porous coatings covering said protuberances. The coatings comprise two layers of substantially spherical particles of the same alloy as the disc body. The coatings can also cover the upper and lower surfaces of the body, in addition to the surfaces of the protuberances. The coatings provide for tissue/bone ingrowth. The disc of this patent does not offer the flexibility of a human disc, either with regard to relative rotation of adjacent vertebrae or with regard to relative axial movement of the vertebrae.

Prior U.S. Pat. No. 4,759,766 discloses an artificial disc comprising first and second end plates and a piece of hard plastic such as polyethylene or polyurethane of high compression and tension strength interposed between the end plates. The end plates can have a number of configurations. The end plates may be provided with teeth to guarantee an anchorage in the opposed vertebrae.

Prior U.S. Pat. No. 4,743,256, in FIG. 12, discloses a plug dimensioned and shaped to fit and maintain the disc space between adjacent vertebrae. Bone piercing tangs penetrate the vertebrae. The plug is preferably made of an inert metal substrate having a porous metal coating thereon.

Prior publication entitled "Characterization of Hexsyn, a Polyolefin Rubber", by McMillian, Journal of Biomaterials Applications, Vol. 2, July, 1987, pages 3–100, discloses a polyolefin rubber for use in biomedical applications. The rubber is biocompatible and fatigue resistant. It is synthesized from 1-hexane with 3–5% methylhexadiene as the source of residual double bonds for vulcanization. A primary use for the rubber components is in ventricular assist and artificial heart systems. This rubber is used as the hinge portion of prostheses, such as finger joints. The Journal article gives a number of physical properties of the material such as tensile strength, elongation and elastic modulus.

SUMMARY OF THE INVENTION

The present invention resides in a resilient, spinal disc prosthesis to replace a damaged or degenerated spinal disc. The prosthesis comprises an upper rigid flat plate, a lower rigid flat plate, and a flat elastomeric core interposed between the rigid plates and adhered to the rigid plates. The rigid plates and elastomeric core are the same size and shape in plan view and thus completely overlie each other. The elastomeric core is a one-piece solid homogeneous piece of material and is not a laminate. There is no connection of the upper and lower rigid plates to each other except by the elastomeric core therebetween. The outer surface of the rigid plates promotes tissue ingrowth. The elastomeric core is made of a polyolefin rubber. The polyolefin rubber has an ultimate tensile strength of about 1,900 psi, an ultimate elongation of about 350% at 37° C. (98.6° F.), and an elastic modulus in the range of about 220–600 psi at 100% elongation and about 610–1,000 psi at 200% elongation and greater than 1,000 psi at 300%. The upper and lower rigid plates are bonded to the elastomeric core during vulcanization of the core with the use of a primer and adhesive. Vulcanization increases the strength of the elastomeric core by increasing the amount of cross-linking of the material. In addition, the elastomer's biostability improves. After vulcanization, the material is thoroughly cleaned to extract any vulcanization chemicals or by-products which may be cytotoxic.

In one embodiment of the present invention, the upper and lower rigid plates are made of a biocompatible metal such as 316 LVM stainless steel or similar stainless steel, unalloyed titanium or a titanium-vanadium-aluminum alloy, a cobalt-chromium alloy or a cobalt-chromium-molybdenum alloy or a cobalt-nickel-chromium-molybdenum alloy. A plurality of spaced-apart projections extend outwardly from the exposed faces of the rigid plates for engagement with vertebrae above and below the rigid plates. The protuberances are a plurality of spaced-apart spikes extending vertically from the outer faces of the rigid plates and are made of the same material as the plates. Preferably, a porous coating of particles of the same material as the rigid plates is adhered to at least the exposed face of each of the rigid plates. The porous coating promotes tissue ingrowth into the plates and thus attachment of the vertebrae to the disc. The rigid plates may also be provided with a porous coating on their inner surfaces. A porous coating on the inner surface of a rigid plate enhances the attachment of the elastomeric core to the rigid plate.

In another embodiment of the present invention, the upper and lower rigid plates are formed by a plurality of layers of biocompatible metal particles such as 316 LVM stainless steel or similar stainless steel, unalloyed titanium or titanium-vanadium-aluminum alloy, a cobalt-chromium alloy or a cobalt-chromium-molybdenum alloy or a cobalt-nickel-chromium-molybdenum alloy. The particles function to provide tissue ingrowth and to enhance the attachment of the elastomeric core to the plates. The number of layers of particles insures the rigidity of the plates.

In another embodiment, the rigid plates are formed as a plastic composite such as an organic matrix bonded to graphite reinforcement fibers. The elastomeric core is adhered to the composite rigid plates.

In view of the fact that the spinal disc of the present invention comprises upper and lower rigid plates bonded to a core of polyolefin rubber, the spinal disc of the present invention will function to:

(1) Transmit load between the vertebrae with an even distribution of the load across the disc.
(2) Act as a shock absorber to attenuate high forces from damaging the surrounding bone or soft tissue.
(3) Enable relative turning of the vertebrae between which the disc is located but in conjunction with the bony anatomy and soft tissue will limit the relative turning to about 2°-3°.
(4) Accommodate bending of the back in various directions but in conjunction with the bony anatomy and soft tissue, will limit the spine to physiologic bending angles.

Also, since the rigid plates may be provided with projections which interlock with the vertebrae, the disc will be maintained in place relative to the vertebrae to prohibit motion until and after the tissue ingrowth coating on the rigid plates enables tissue to grow into the disc. These are some of the important features of the disc of the present invention.

BRIEF DESCRIPTION OF THE DRAWINGS

Further features of the present invention will become apparent to those skilled in the art to which the present invention relates from reading the following specification with reference to the accompanying drawings, in which:

FIG. 1 is an elevation view of a human spinal column having an artificial disc in accordance with that of the present invention placed therein;

FIG. 2 is a perspective view of the artificial spinal disc of FIG. 1;

FIG. 3 is a plan view looking at the spinal disc of FIG. 2 from the top;

FIG. 4 is a cross sectional view of the spinal disc of FIG. 2 taken along line 4—4 of FIG. 2;

FIG. 5 is a sectional view of another embodiment of the invention; and

FIG. 6 is a sectional view of still another embodiment of the invention.

DESCRIPTION OF A PREFERRED EMBODIMENT

The present invention relates to an artificial spinal disc to replace a damaged spinal disc in a human. The artificial spinal disc of the present invention acts much like a natural spinal disc. Yet, the spinal disc of the present invention is simple in construction, easy to manufacture, and quite effective in the human body. One embodiment of the present invention is illustrated in FIGS. 1-4 and is designated 5. In FIG. 1, the disc 5 is illustrated in position between upper and lower vertebrae 6, 7 of a human.

The disc 5 comprises an upper rigid flat plate 12, a lower rigid flat plate 14, and a flat elastomeric core 16 interposed between the two rigid plates 12, 14 and adhered to the two plates 12, 14. In the illustrated embodiment, the elastomeric core is of uniform thickness and thus the rigid plates 12 and 14 extend parallel to each other. However, it is contemplated that the core may be wedgeshaped in cross-section and thus the plates 12 and 14 would not be parallel. The plates 12, 14 are interconnected only by the core 16. There is no other connection of the plates 12, 14. Further, the core 16 is a one-piece solid homogeneous material and is not a laminate.

The plates 12 and 14 are preferably kidney-shaped in plan with a rounded convex side 18 (FIG. 3) and an opposed concave side 20 (FIG. 3) separated by relatively straight sides 22 and 24 (FIG. 3). The concave side could be straight if desired. The configuration shown in FIG. 3 is designed to conform generally to the shape of a natural disc. Further, the dimensions of the plates 12 and 14 are identical. The dimensions of the core 16 in plan view is identical to the dimensions of the plates 12 and 14 in plan view. Thus, the rigid plates 12 and 14 and core 16 completely overlie each other, and the rigid plates 12 and 14 do not extend beyond the core 16 nor does the core 16 extend beyond the rigid plates 12, 14. The thickness of the core 16 may vary depending upon the size of the separation of the vertebrae between which the disc 5 is to be placed, and the size may vary depending upon the size of the patient.

The rigid flat plates 12 and 14 in the embodiment of FIGS. 1-4 are made of a metal material. The thickness of the plates 12 and 14 may typically be about 0.039 inches. The material of which the plates 12 and 14 is made may be radio-opaque, that is, observable by means of X-ray. Suitable biocompatible materials are 316 LVM stainless steel or similar stainless steel, unalloyed titanium or a titanium-vanadium-aluminum alloy or a cobalt-chromium alloy or a cobalt-chromium-molybdenum alloy or a cobalt-nickel-chromium-molybdenum alloy.

The elastomeric core 16 is a vulcanizable material having flexure properties closely duplicating those of a human disc. Broadly, the elastomeric material can be characterized as relatively stiff, that is, with only small flexion and compressibility under load, but sufficient flexion and compressibility to meet the requirements for duplicating a natural disc. More specifically, the elastomeric core provides a torque rotation angle of about 2° to 3° necessary to accommodate normal activity. A similar axial resiliency is provided to permit stooping over, body extension, and bending in various directions. At the same time, the disc 5 is capable of maintaining a desired separation between adjacent vertebrae under normal loading. The disc also acts as a shock absorber to attenuate high forces from damaging the surrounding bone or soft tissue.

The elastomeric material 16, which meets these requirements, is a polyolefin rubber marketed by Goodyear Tire and Rubber Company under the trademark Hexsyn. This rubber is synthesized from 1-hexene with 3-5% methylhexadiene as the source of residual double bonds for vulcanization. This rubber is disclosed in the aforementioned journal of Biomaterials Applications by McMillian. The disclosure of this publication is incorporated by reference herein.

The most common test for evaluating elastomeric materials are the tests for ultimate tensile strength, which is a measure of tensile load at which the material fails; ultimate elongation, which is the amount the elastomer can be stretched before it fails; and the elastic modulus which is a measure of the stiffness or rigidity of the material. All of these values can be obtained using a standard tensile testing machine following ASTM guidelines.

Using the above test and as reported in the aforesaid publication, the material of the core 16 has tensile strengths ranging from about 1,700 psi to about 2,500 psi. The material of the core 16 has an ultimate elongation value of about 230% to about 360% at 37° C. (98.6° F.), with an average of about 295%. In other words, the material stretches 230% to about 360% at 37° C. before failure. The material of the core 16 also has a modulus of elasticity value of about 200 psi to about 620 psi to effect about 100% elongation of the material, and values of about 540 psi to about 1,000 psi at 200% elongation, and over 1,000 psi at 300%. This means that by applying a force per unit of area of 200-540 psi to the material, it will stretch 100% and by applying a force per unit of area of about 540 psi to 1,000 psi, it will stretch 200%, and applying a force per unit of area in excess of 1,000 psi will cause the material to stretch at least 300%.

Based on the above, and other observations and data, it has been determined that the elastomeric core material should have an ultimate tensile strength of about 1,900 psi, an ultimate elongation of about 350% at 37° C. (98.6° F.), and an elastic modulus in the range of about 220-600 psi at 100% elongation and about 610-1,000 psi at 200% elongation, and greater than 1,000 psi at 300% elongation. Such a material provides a desired degree of resilience, and at the same time, sufficient resistance to compression to maintain vertebrae separation, to meet the requirements of every day activity when used in a human.

From the above data, it can be seen that Hexsyn provides excellent properties for use in an artificial disc. Vulcanization increases the mechanical properties of the disc as well as its biostability.

The elastomeric core is bonded to the plates 12 and 4 by a bond having sufficient strength to withstand any relative turning motion imposed upon the prosthesis, such as turning movement of the vertebra contiguous with the top plate 12 relative to the vetebra contiguous with the bottom plate 14; for instance, 2°-3° of movement. Preferably, the rubber is bonded to the plates 12 and 14 in the vulcanization process particularly due to the use of a primer and adhesive. The inner surface of the plates 12 and 14 can be provided with a porous coating 20 which comprises metal particles deposited by some known technique such as plasma spraying or vapor deposition on the inner surface of plates 12, 14 which particles are of the same material as the plate. These particles interlock with the material of the core 16 to provide a strong bond between the plates 12 and 14 and the core 16. Alternatively, the rubber can be adhered to the plates 12 and 14 subsequent to vulcanization, by a suitable high strength adhesive.

The top and bottom plates 12 and 14 are covered on their exposed faces with a porous coating 26 comprising layers of small spherical particles. Preferably, the particles are of the same material as the plates. Particles can be applied to the plates by vapor deposition, by plasma jet spraying, or by any other suitable known technique. The coating should be firmly adhered to the plates 12, 14 and incapable of removal by normal abrasion. The porous coating 26 provides for ingrowth of tissue to cause the bone to more firmly attach to the plates 12, 14 than if the coating 26 was not present.

Both the top and bottom plates 12, 14 are provided, on their exposed faces, with a plurality of projections or spikes 28 which are spaced apart and extend vertically outwardly from the plates. In the embodiment illustrated in FIGS. 1-4, the projections are conical in configuration and hollow. The projections have an opening 29 at the apex conical shape communicating the interior of the projection with the exterior thereof. They preferably are also of the same material as the plates 12, 14, and may be welded, brazed, or otherwise firmly bonded to the plates. The projections are adapted to fit within seats or depressions formed in the opposed vertebra, and should be sufficiently well bonded to the plates to withstand 2°-3° relative turning movement of adjacent vertebrae. The projections position the disc 5 relative to the vertebrae and function to maintain that position. Preferably, the projections are not covered with a porous coating such as 26. In this way, the projections can be made to fit closely and snugly within seats or depressions formed in the opposing vertebrae. However, they may be covered with the porous coating.

The conical shape and hollow configuration of the projections or spikes provides the artificial disc 5 with substantial stability in connection with normal activity of the individual fitted with the artificial. disc until and after the tissue ingrowth coating on the rigid plates enables tissue to grow into the disc.

The core of elastomeric material 16 provides a degree of resiliency and flexibity closely matching that of a human disc. Its thickness can be varied to accommodate an individual's requirements. The disc permits substantially universal movement of adjacent vertebrae including tilt of one vertebra with respect to the other, relative axial movement, relative transverse movement, and rotational movement. The use of opposed rigid plates on opposite sides of the elastomeric core, protect the elastomeric material from wear and degradation by providing for an even distribution of load through the disc.

FIG. 5 shows a modified embodiment of the present invention. The disc in FIG. 5 is identical to the disc described above and shown in FIGS. 1-4. The disc of FIG. 5 is generally designated by the reference numeral 50. The disc 50 includes an upper rigid plate 51 and a lower rigid plate 52 separated by and adhered to a core of polyolefin rubber 53. The single difference between the disc of FIG. 5 and the disc of FIGS. 1-4 is that the rigid plates 51 and 52 in the embodiment of FIG. 5 are completely made of layers of metal particles. These layers are deposited on each other by vapor deposition or by a plasma spray technique or by any other suitable technique. The layers of particles are made of any of the materials of which the plates in the embodiment of FIGS. 1-4 may be made. The various layers of particles provide sufficient rigidity for the plates 51 and 52 to provide for even distribution of the load through the disc.

FIG. 6 shows still another embodiment of the present invention. In the embodiment of FIG. 6, the rigid upper and lower plates are designated 60 and 61, and the polyolefin rubber core is designated 62. The structure of the disc of FIG. 6 is identical to the structure of the disc of FIGS. 1-4 except that the plates 60 and 61 in the embodiment of FIG. 6 are made of a non-metallic composite material, such as a plastic composite made of an organic matrix reinforced with graphite fibers. Even though the material of plates 60 and 61 is plastic, it is a rigid material capable of transmitting the load uniformly through the disc. Since the material is a plastic material, it is radiolucent, i.e., capable of partially transmitting X-rays therethrough. The radiolucency will permit the surgeon to view the interface between the bone and plates to determine if tissue ingrowth is occurring. In this case, the projections, such as projections 26, may still be used even though they are not shown in FIG. 6. The projections on the plates 60, 61 could be formed or molded with the plates 60, 61 as an integral part of the plates 60, 61. Further, the core 62 can be bonded to the plates 60, 61 in any suitable manner.

From the above description of a preferred embodiment of the invention, those skilled in the art will perceive improvements, changes and modifications therein. Such improvements, changes and modifications within the skill of the art are intended to be covered by the appended claims.

Having described a preferred embodiment of the invention, I claim:

1. A spinal disc prosthesis to replace a damaged spinal disc comprising:
    an upper flat rigid plate;
    a lower flat rigid plate;
    an elastomeric core interposed between said plates and adhered to said plates, said elastomeric core consisting of a one-piece solid homogeneous elastomeric material, free of any cavity therein; and
    said elastomeric core being made of an elastomeric polyolefin rubber, said elastomeric polyolefin rubber having an ultimate tensile strength of about 1,900 psi and ultimate elongation of about 350% at 37 degrees C (98.6 degrees F.), and an elastic modulus in the range of about 220-600 psi at 100% elongation and about 610-1,000 psi at 200% elongation and greater than 1,000 psi at 300% elongation.

2. A spinal disc prosthesis as defined in claim 1, comprising a plurality of spaced-apart protuberances extending outwardly from outer faces of said plates for engagement with vertebrae above and below said plates to fix said plates and core in position relative to said vertebrae, said plates being made of a biocompatible material, inner faces of said plates being coated with a porous particle coating, said coating being porous to facilitate adherence of said elastomeric core to said plates, and said plates being connected together only by said core.

3. A spinal disc prosthesis as defined in claim 2 wherein said elastomeric polyolefin rubber is synthesized from 1-hexene with 3-5% methylehexadiene as a source of residual double bonds for vulcanization.

4. A spinal disc prosthesis as defined in claim 1 wherein said elastomeric polyolefin rubber is synthesized from 1-hexene with 3-5% methylhexadiene as a source of residual double bonds for vulcanization.

5. A spinal disc prosthesis to replace a damaged spinal disc comprising an upper flat rigid plate, a lower flat rigid plate, an elastomeric core interposed between said plates and adhered to said plates, said elastomeric core consisting only of a one-piece solid homogeneous elastomeric material, free of any cavity therein, said elastomeric material being an elastomeric polyolefin rubber said plates being connected only by said core, and a plurality of spaced-apart protuberances extending outwardly from said plates for engagement with vertebrae above and below said plates to fix said plates and core in position relative to said vertebrae, said elastomeric polyolefin rubber being synthesized from 1- hexene with 3-5% methylhexadiene as a source of residual double bonds for vulcanization.

6. A spinal disc prosthesis as defined in claim 5, wherein said plates are made of a biocompatible metal material, inner faces of said plates being coated with a porous particle coating of the same material as said plates, said coating being porous to facilitate adherence of said elastomeric core to said plates.

* * * * *